United States Patent
Wendelstorf et al.

(10) Patent No.: US 7,435,245 B2
(45) Date of Patent: Oct. 14, 2008

(54) FASTENING ELEMENT FOR HYGIENE ARTICLES AND ENDLESS TAPE FOR THE PRODUCTION OF SAID ELEMENT

(75) Inventors: Carsten Wendelstorf, Ulm (DE); Rainer Mangold, Herbrechtingen (DE)

(73) Assignee: Paul-Hartmann AG, Heidenheim (DE)

( * ) Notice: Subject to any disclaimer, the term of this patent is extended or adjusted under 35 U.S.C. 154(b) by 157 days.

(21) Appl. No.: 10/485,591

(22) PCT Filed: Jun. 24, 2002

(86) PCT No.: PCT/EP02/06945

§ 371 (c)(1),
(2), (4) Date: Feb. 2, 2004

(87) PCT Pub. No.: WO03/015683

PCT Pub. Date: Feb. 27, 2003

(65) Prior Publication Data
US 2004/0194260 A1 Oct. 7, 2004

(30) Foreign Application Priority Data
Aug. 18, 2001 (DE) .............................. 101 40 621

(51) Int. Cl.
*A61F 13/15* (2006.01)
*A44B 1/04* (2006.01)

(52) U.S. Cl. .................... 604/391; 604/385.03; 24/442

(58) Field of Classification Search .......... 604/385.03, 604/386, 387, 389, 391, 385.04; 24/306, 24/442–452

See application file for complete search history.

(56) References Cited

U.S. PATENT DOCUMENTS

| 3,999,544 | A |   | 12/1976 | Feldman et al. |
| 4,158,363 | A | * | 6/1979  | Schaar .................. 604/390 |
| 4,177,812 | A | * | 12/1979 | Brown et al. ............ 604/390 |
| 4,237,890 | A | * | 12/1980 | Laplanche .............. 604/390 |

(Continued)

FOREIGN PATENT DOCUMENTS

DE 7413121 4/1974

(Continued)

OTHER PUBLICATIONS

Automated translation of DE19814277 available at esp@cenet.*

(Continued)

*Primary Examiner*—T. Zalukaeva
*Assistant Examiner*—Michael G Bogart
(74) *Attorney, Agent, or Firm*—YoungBasile

(57) ABSTRACT

A fastening element for hygiene articles. The fastening element presents a first longitudinal direction and a second transverse direction in the form of a longitudinal section. The fastening element includes mechanically adhering clip elements, a first section corresponding to a first support layer and a second section corresponding to a second support layer. The first section contains a first zone by which the fastening elements are attached to the hygiene article. The second section contains a second zone arranged outside of the first section in the transverse direction in which the clip elements are provided. The element is folded in a zigzag manner along longitudinal folding lines and the second zone with the mechanically adhering clip elements lies outside of the zigzag folded configuration in the transverse direction.

15 Claims, 3 Drawing Sheets

U.S. PATENT DOCUMENTS

| | | | |
|---|---|---|---|
| 4,576,598 A * | 3/1986 | Tritsch | 604/390 |
| 4,670,012 A | 6/1987 | Johnson | |
| 5,234,517 A | 8/1993 | Pape et al. | |
| 5,591,521 A * | 1/1997 | Arakawa et al. | 428/352 |
| 5,624,428 A * | 4/1997 | Sauer | 604/391 |
| 6,030,373 A | 2/2000 | VanGompel et al. | |
| 6,039,906 A * | 3/2000 | Sageser et al. | 264/156 |
| 6,363,587 B1 * | 4/2002 | Richter et al. | 24/306 |
| 6,451,000 B1 * | 9/2002 | Hayase et al. | 604/385.13 |
| 6,524,294 B1 * | 2/2003 | Hilston et al. | 604/386 |
| 6,526,631 B1 * | 3/2003 | Alberg et al. | 24/306 |
| 6,579,275 B1 * | 6/2003 | Pozniak et al. | 604/390 |
| 6,656,171 B1 * | 12/2003 | Matsuda et al. | 604/390 |
| 2004/0236301 A1 * | 11/2004 | Wendelstorf et al. | 604/387 |
| 2005/0143709 A1 * | 6/2005 | Lindstrom | 604/391 |

FOREIGN PATENT DOCUMENTS

| | | |
|---|---|---|
| DE | 198 14 277 A1 * | 11/1999 |
| DE | 200 05 920 | 6/2000 |
| EP | 0 292 970 | 11/1988 |
| EP | 1 151 736 | 11/2001 |
| FR | 2267058 | 11/1975 |
| FR | 2 267 517 | 8/1993 |
| GB | 1 441 567 | 7/1976 |
| WO | WO 98 22069 | 5/1998 |

OTHER PUBLICATIONS

Translation of International Preliminary Examining Report for PCT/EP2002/006945 provided by WIPO.*

Machine-generated translation of DE 20005920 U provided by the EPO.*

English language abstract for EP 1151736.*

* cited by examiner

FASTENING ELEMENT FOR HYGIENE ARTICLES AND ENDLESS TAPE FOR THE PRODUCTION OF SAID ELEMENT

BACKGROUND

The invention relates to a fastening element for hygiene articles, particularly for diapers or for incontinence articles, for releaseable closing the article when worn by a user, where the fastening element has a first longitudinal direction and a second transverse direction and has been severed from a continuous web in the form of a longitudinal section. The fastening element is configured with mechanically acting closures, having a first section of a first supporting layer and a second section of a second supporting layer which is disposed in a transverse direction next to the first section and is attached thereto, and where the first section has a first zone with which the fastening element can be attached to the hygiene article, and where the second section has a second zone disposed in the transverse direction outside the first section and in which the mechanically acting closures are furnished, and where the fastening element is folded in the longitudinal direction.

Such a fastening element is known, for example, from WO 95/16425 and from EP 0 669 121 A1.

Moreover, non-generic fastening elements with adhesive closures are known from U.S. Pat. No. 4,237,890, which elements however possess the remaining aforementioned generic features and are folded in a "Z" shape. The folding is carried out in such a way that adhesively configured zones end up on top of each other.

With the various aforementioned known fastening elements as the point of departure, the object of the present invention is to improve fastening elements of the generic type with regard to the following aspects.

When fastening elements are attached to hygiene articles during the production of the hygiene articles, the problem always arises of keeping the fastening elements in the assembled position, particularly when the hygiene article is folded in an often complex manner following the attachment and packaged. During the subsequent handling during production of the hygiene article, there is often a problem with the fastening elements becoming detached or unfolding. The intention of the present invention is to bring about improvement in this regard.

Furthermore, the manageability of the fastening elements, both before and during attachment to a hygiene article, and the ease of affixation itself is to be simplified, keeping the available volume that a plurality of fastening elements occupies as small as possible.

SUMMARY

A generic fastening element under the present invention is provided by folding the fastening element in a Z-shape, with fold lines running in the longitudinal direction, and locating the second zone with the mechanically acting closures in the transverse direction outside the folded, Z-shaped configuration.

The invention thus proposes to create a Z-shaped fold of this kind and to furnish the mechanically acting closures in a second section of the second supporting layer so that they end up outside the folded, Z-shaped configuration. This has various advantages during the manufacture of the fastening elements themselves and during the handling and attachment of the fastening elements to hygiene articles: Because the mechanically acting closures, which are usually formed by one component of a hook-and-loop material, end up outside the folded, Z-shaped configuration, there is no risk that unfolding the fastening elements when used as intended in a hygiene article will be hampered by the fastening elements becoming entangled in the Z-shaped fold. A further considerable advantage can also be seen in the fact that the mechanically acting closures no longer obtrusively stack up perpendicular to the plane of the web, but can be configured such that the thickness of the second section of the fastening elements in the area of the closures is no greater than in the area of the folded, Z-shaped configuration. Furthermore, this opens up the possibility that the mechanically acting closures, with the fastening elements attached to the hygiene article, coact adhesively with one surface of the hygiene article such that it prevents the fastening elements from becoming detached. If the mechanically acting closures of the fastening elements are configured, for example, as the hook component of a hook-and-loop material, the hooks can coact adhesively with a textile outer covering of a fluid-impervious outer layer or with a textile component of an inside of the hygiene article.

In a further aspect of the invention, it proves advantageous if a fold line running in the longitudinal direction runs at least in sections along a material transition between the first and the second section. If a material transition was mentioned previously, this can be understood to mean, for example, an overlap area between the first and the second supporting layer. It would also be conceivable for the first and second supporting layers to butt or to be disposed at a relatively small distance from each other and be joined together by means of a third, specifically strip-shaped, connecting element. In this case, the fold line could run along a material transition between the first or second section and this connecting element. In each instance, ease of folding is thereby simplified and the accumulated thickness in the area of the folded, Z-shaped configuration is kept as small as possible. Advantageously the fold line runs immediately along a longitudinal edge of the second section. This proves particularly advantageous, specifically when the first and the second section (prior to folding) are overlapped in the transverse direction and are joined in the overlap area in any manner chosen. The joining processes in question are welding processes or adhering procedures in the broadest sense which effect a joint between the materials with or without inclusion of an additional joining material.

Furthermore, to create the Z-shaped fold it is proposed that an additional longitudinal fold line run immediately along a longitudinal edge of the first zone with which the first section of the fastening element is joined to a hygiene article. This zone is advantageously formed by an adhesive coating, either a permanent adhesive or pressure-sensitive adhesive, which is applied perpendicular to the plane of the web. It thus proves advantageous if the additional fold line, at least in sections, runs along a longitudinal edge of this second zone.

It further proves advantageous if the second supporting layer comprises an essentially inelastic material and is essentially not extensible in the transverse direction. For example, the second supporting layer could be made from a thermoplastic material and/or a nonwoven which is specifically and preferably thermally bonded, for example, has a weld or embossed pattern formed from discrete spots of glue. It can also be a layer of plastic film which is preferably essentially non-extensible at least in the transverse direction.

The first supporting layer forming the first section of the fastening element preferably comprises a material which is elastically extensible at least in the transverse direction and is preferably configured elastically extensible in this transverse direction. Elastically extensible is understood to mean a web material which can be stretched by at least 1.2 times its original dimension when tension is applied and which, when tension is removed, contracts again at least far enough to nullify at least half of the stretched length. Of course, materials are known and preferred for use as the first supporting layer which demonstrate much more pronounced elastic retraction characteristics.

To achieve these elastically extensible properties in the first supporting layer, elastic nonwoven materials can be used to advantage, or so-called "stretchbond" laminates with one or more nonwoven layers.

In a further aspect of the invention, the folded, Z-shaped configuration is secured to itself, which can be achieved specifically with spots of glue or weld spots or by needling processes. It proves expedient to releasably stabilize the folded, Z-shaped configuration with discrete securing points, from 1 to 10 in number, preferably 3 to 5, where the securing points have a cross-sectional area of less than 1 mm$^2$.

In accordance with a further inventive concept of significance, the folded, Z-shaped configuration is attached to itself when the longitudinal sections are cut from the continuous web in the transverse direction, thereby creating a cut edge; fibers from the layers folded over on one another are worked into or pulled into the layer disposed below, i.e. partially pulled out of one layer and introduced into the second layer. The effect achieved thereby could in the broadest sense be compared with needling fibrous nonwoven materials. When cutting the longitudinal sections, specifically by performing a "crush cut," fibers from one layer are pulled into the layer disposed thereunder in the direction of the cut. This "crush cut" is preferably performed by a compliant knife, specifically a knife under pretension, or at least mounted to yield a small amount. This knife is preferably disposed on a rotating cylinder and, when performing the cut, can be positioned under suitable pressure against a counter cylinder over which the web is guided and which forms an anvil for the knife.

In accordance with a further inventive concept, a pull tab for the user to grip with a finger is provided in the transverse direction outside the second zone and on the side of the second zone facing away from the first section. No closures are provided on this pull tab. It is advantageously formed by the second supporting layer of the second section itself.

During manufacture and also during the handling of the fastening element under the invention, it proves advantageous if the first zone and the second zone are furnished on the same side of the continuous web. The Z-shaped fold is preferably of such a nature that the first zone and the second zone are furnished on the same visible side of the folded fastening element.

The present invention has furthermore as its subject a continuous web for the manufacture of the previously described fastening elements of the invention, which are severed as longitudinal sections from this continuous web in the transverse direction. This continuous web is characterized in that it is wound in the form of a roll with the folded, Z-shaped configuration.

The continuous web can be wound in such a way that the width of the coil is determined by the extension of the fastening elements in the transverse direction, or the continuous web is cross-wound so that the width of the coil is substantially greater than the transverse extension of the fastening elements.

The advantage of the fastening elements under the invention and the winding of the continuous web in accordance with the invention is that the thickness of the second section of the fastening elements with the mechanically configured closures in the second zone does not build up in an obtrusive fashion, but rather that it is possible to select the thickness of this second section in the area of the closures to be less than or essentially to correspond to the thickness of the fastening element in the area of the folded, Z-shaped configuration.

In accordance with a further inventive concept, it proves advantageous if, in the case of fastening elements with an adhesive application in the first zone, the continuous web is wound in such a way that, during the winding, the glue in the first zone ends up on the second section and is easy to release when the web is unwound. It would certainly also be conceivable that this adhesive application could be furnished with a release coating, but this would mean the use of an additional layer. To this extent it proves advantageous if the adhesive application and a corresponding strip-shaped area of the second section, preferably unbroken in the longitudinal direction, or its surface respectively, is configured such that it is possible to release the glue in the first zone easily without harming the adhesive coating itself.

If a first section and a second section of the fastening element connected to each other as discussed in the preceding, it must be pointed out that the Z-shaped fold in conjunction with the arrangement of the second zone carrying the closures in the transverse direction outside the folded, Z-shaped configuration is regarded as independently inventive, even if the fastening element is configured in one piece in place of the first and second sections.

BRIEF DESCRIPTION OF THE DRAWING

Additional features, details and advantages of the invention will be better understood from the appended patent claims and the illustrative drawings and subsequent description of a preferred embodiment of the fastening element under the invention. In the drawings:

DETAILED DESCRIPTION

Figure 1:
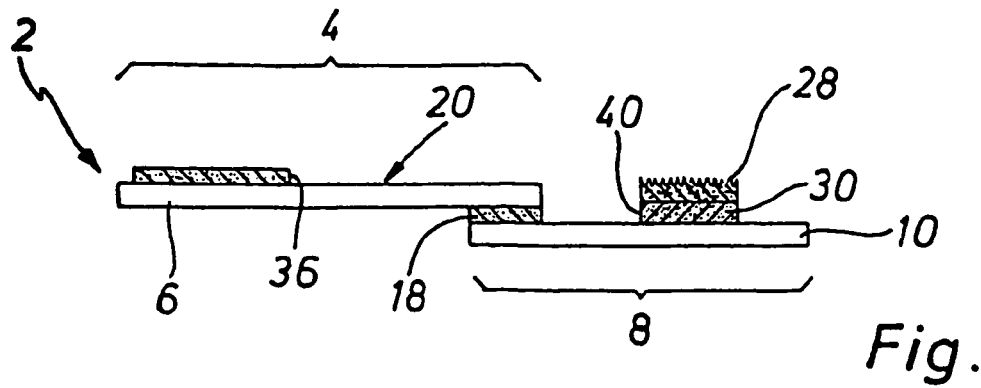
FIG. 1 shows a cross-sectional view of one aspect of a fastening element under the invention.
Figure 2:
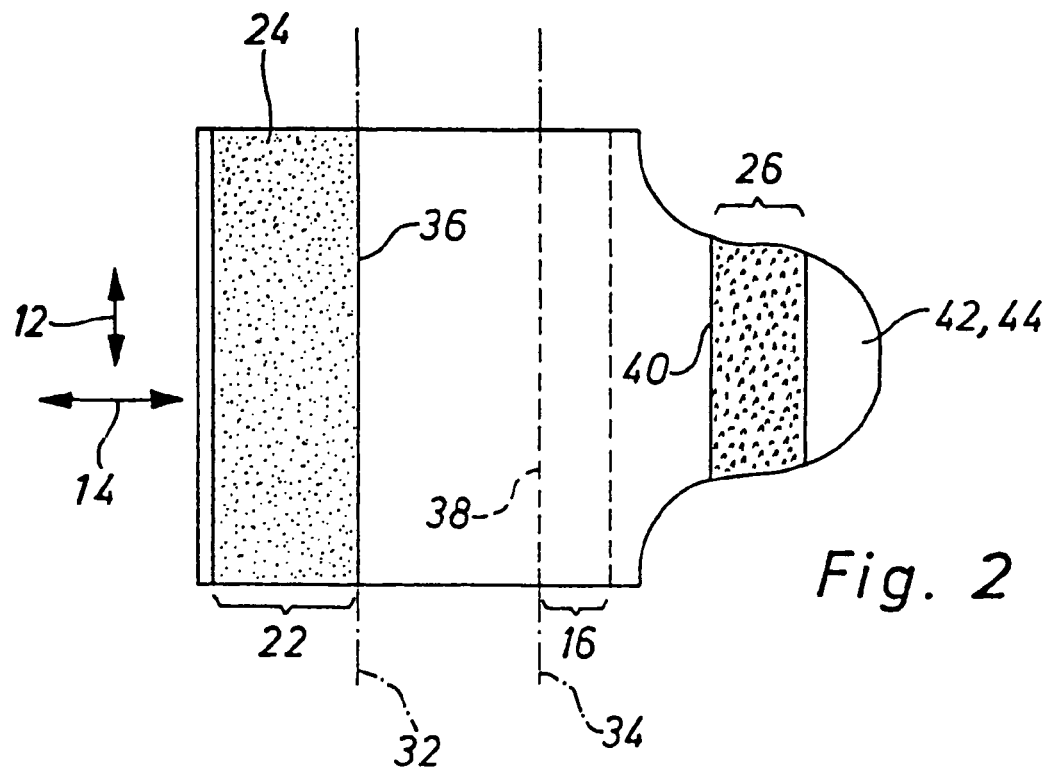
FIG. 2 shows a plan view of the fastening element from FIG. 1.

FIGS. 1 and 2 show a fastening element in accordance with the invention identified overall with the reference number 2. The fastening element 2 comprises a first section 4 of a first supporting layer 6 and a second section 8 of a second supporting layer 10.

The fastening element 2 has been severed from a continuous web as a longitudinal section, where the continuous web extends in a first longitudinal direction 12. The second section 8 is disposed in a transverse direction 14 next to the first section 4, where in the instance shown the first section 4 and the second section 8 overlap one another, so that an overlap zone 16 is formed to which the two sections 4, 8 are permanently joined by means of an adhesive 18, weld points or in some other way.

On a first top side 20 of the first section 4 provision is made for a first zone 22 having an adhesive coating 24 with which the fastening element 2 can be attached to a hygiene article.

In a second zone 26 of the second section 8, provision is made for mechanically acting closures 28, preferably in the form of a hook component of a hook-and-loop material, specifically adhered by means of an adhesive 30. The second zone 26 is preferably furnished on the same top side 20 of the fastening element 2 as the first zone 22.

Figure 3:
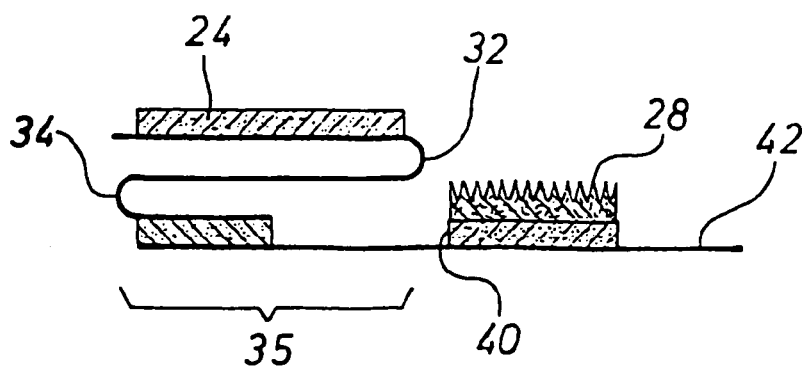
FIG. 3 shows a cross-sectional view of the folded, Z-shaped fastening element from FIGS. 1 and 2.

Furthermore, first and second fold lines 32, 34 are indicated in FIG. 2 and can be seen in FIG. 3 around which the fastening element 2 is folded in a Z-shape in the longitudinal direction 12, so that the configuration 35 shown in FIG. 3 is created. Advantageously the first fold line 32 runs immediately along a longitudinal edge 36 of the adhesive coating 24 in the first zone 22. The second fold line 34 advantageously runs immediately along the material transition between the first and second section 4 or 8, i.e., along one edge 38 of the overlap zone 16.

As is apparent from FIG. 3, the second zone 26 of the second section 8 is spaced at such distance in the transverse direction 14 from the overlap zone 16 or from any other material transition area between first section 4 and second section 8 that it is located outside the folded, Z-shaped configuration 35 of the fastening element 2 in the transverse direction 14, which proves to be advantageous in several respects. In the instance shown, a longitudinal edge 40 of the second zone 26, and consequently of the mechanically acting closures 28 facing the first section 4, extends almost to the first fold line 36 in the case of the folded, Z-shaped configuration 3. It would also be conceivable that the second zone 26 is positioned with respect to the second section 8 in such a way that the mechanically acting closures 28, or their longitudinal edge 40, are spaced a few millimeters from the folded, Z-shaped configuration 35 of the fastening element.

When the fastening element with its touch-sensitive adhesive application 24 in the first zone 22 is applied to a hygiene article, the second zone 26 with the mechanical closures 28 is, as already mentioned, disposed outside the folded, Z-shaped configuration 35 and can thus serve to secure the fastening element or the second section 8 to a textile surface on a hygiene article. Securing the second section 8 in this way is intended solely to secure the fastening element during manufacture and packaging until application of the hygiene article to a wearer, at which point at the latest this connection is released. A user reaches with his fingers between the top side of the hygiene article and a free end area 42 of the second section 8, which acts as a pull tab 44.

It should be mentioned that the first section 4 is configured to be elastically extensible in the transverse direction 14 and that the second section 8 is essentially non-extensible in the transverse direction 14.

An adhesive coating on the first zone 24 and mechanically acting closures in the second zone 26 can be applied uninterruptedly and continuously in the longitudinal direction 12 on a corresponding continuous web of the first supporting layer 6 and the second supporting layer 10. In matching fashion, the first and second support layers 6, 8 are joined continuously by a continuous strip of adhesive 18 or in another fashion in the longitudinal direction 12. Simultaneous production of two symmetrically, but offset in the longitudinal direction by π/2, as known for example from EP 0 669121 A1, is also conceivable and advantageous.

Figure 4:
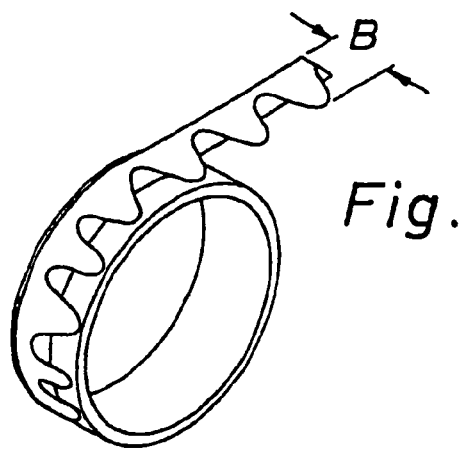
FIG. 4 shows an isometric view of a continuous web wound on a roller.
Figure 5:
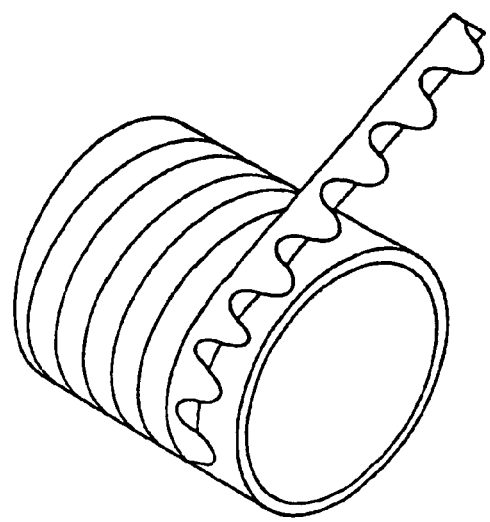
FIG. 5 shows an isometric view of a continuous web wound on a roller, where a cross winding is being made.

Finally, FIGS. 4 and 5 each show a continuous web with fastening elements in a coiled form not yet severed in the transverse direction 14 as longitudinal sections, where FIG. 5 show a cross winding in which the width of the coil is substantially greater than the specific width or transverse extent of the individual fastening elements 2. Greater overall winding stability is achieved thereby and larger quantities of fastening elements can be wound on a single roll and kept in readiness for a production process.

Figure 6:
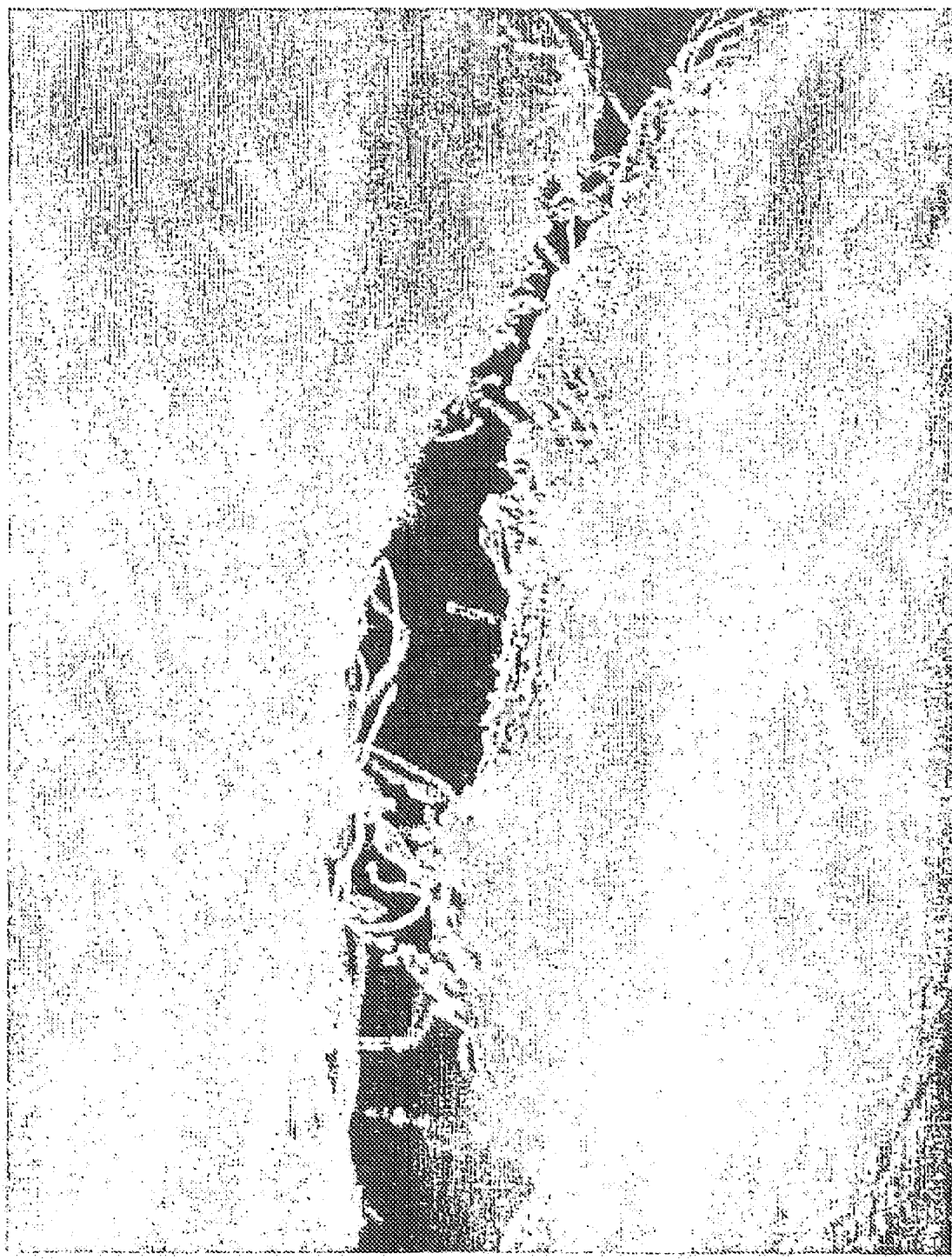
FIG. 6 shows a photographic rendering of the cut edge of the folded Z-shaped fastening element observed in the epimicroscope.

To secure the fastening elements 2 in a folded, Z-shaped configuration 35, it is conceivable to furnish discrete securing points, such as weld points, which join the Z-shaped layers of the fastening elements 2 folded over on each other to each other. However, it has been shown that the folded Z-shaped configuration 35 can be secured in a way that satisfies requirements when the longitudinal sections forming the specific fastening elements are severed from a continuous web; fibers are pulled from the layers disposed above one another in the Z-shape into the layer lying thereunder, so that a form of needling effect is achieved which secures the Z-shaped configuration 35 releasably to itself. This is shown in FIG. 6.

Figure 7:
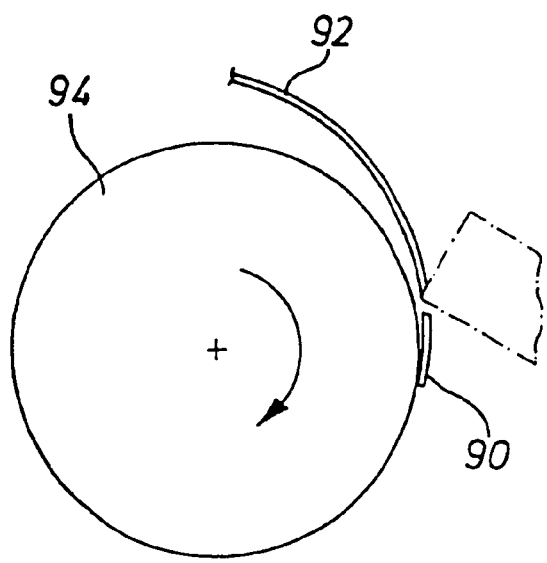
FIG. 7 shows a schematic representation of a cutting device for severing individual folded Z-shaped fastening elements.
Figure 7:
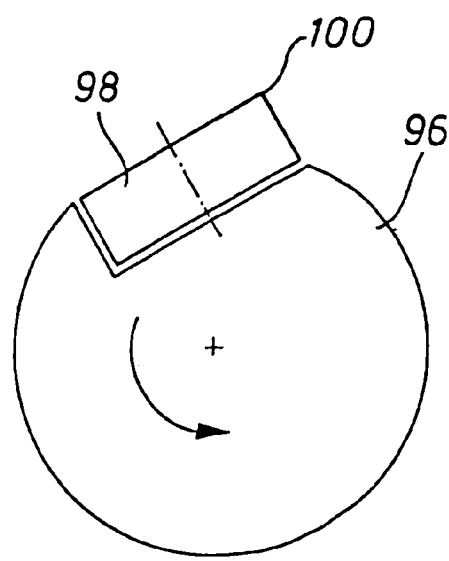

FIG. 7 shows a schematic representation of a cutting device for severing longitudinal sections 90 from a continuous web 92, which also has the folded, Z-shaped configuration 35 for creating the fastening elements. The cutting device comprises an anvil roller 94 across which the continuous web 92 is passed and a knife cylinder 96 having a knife 98 which is under pre-tension and mounted in a floating manner or is intrinsically compliant, with a cutting edge 100. To perform the cut, the knife roller 96 is positioned opposite the anvil roller 94 in such a manner that the cutting edge 100 of the knife 98 touches the surface of the anvil roller 94 and can retract slightly. The continuous web 92 is thus contacted over a relatively short circumferential area by the cutting edge 100 of the knife 98. In contrast to merely shearing, when a "crush cut" is performed, fibers of the layers overlaid on each other are hereby deflected out of one layer and pulled, crushed or worked into the layer thereunder, so that in the severed longitudinal section 90 the layers folded over on each other in a Z-shape are at least slightly connected to each other and unintentional unfolding thereby prevented.

What is claimed is:

1. A roll of fastening elements for releasably closing of hygiene articles when worn by the user and produced on a continuous web, wherein the roll comprises:
    fastening elements each having a respective longitudinal section of the continuous web with a first lengthwise direction and a second transverse direction;
    mechanically acting closures;
    the fastening elements having a first section of a first supporting layer and a second section of a second supporting layer which is disposed in a transverse direction next to the first section and is connected thereto;
    the first section having a first zone configured for non-detachably attaching the fastening elements to the hygiene article and the second section having a second zone located in the transverse direction outside the first section in which the mechanically acting closures are disposed;
    the second section further having a pull tab, the pull tab being graspable by a user to releasably close the hygiene article;
    the first section being folded in a lengthwise direction in a Z-shape with fold lines running in the lengthwise direction, so that pulling the pull tab in the second transverse direction causes the folded, Z-shaped configuration to unfold and to extend in this second transverse direction;
    the second zone having the mechanically acting closures lying outside the folded, Z-shaped configuration in the transverse direction;

wherein the pull tab is located adjacent to the mechanically acting closures in the transverse direction opposite the folded, Z-shaped configuration;

the fastening elements severable from the continuous web in the transverse direction as longitudinal sections thereof; and the continuous web with the folded, Z-shaped configuration wound to form the roll.

2. The roll in accordance with claim 1, wherein;

the first and second sections of the fastening element are overlapped in the transverse direction and are joined in an overlap zone.

3. The roll in accordance with claim 1, wherein a fold line running in the longitudinal direction runs at least in sections along a material transition between the first section and the second section.

4. The roll in accordance with claim 1, wherein the fold line runs immediately along one longitudinal edge of the second section.

5. The roll in accordance with claim 1, wherein a fold line running in the longitudinal direction runs immediately along one longitudinal edge of the first zone.

6. The roll in accordance with claim 1, wherein the second supporting layer comprises an essentially inelastic material and is configured essentially not extensible in the transverse direction.

7. The roll in accordance with claim 1, wherein the first supporting layer comprises a material elastically extensible in at least the transverse direction and is configured elastically extensible in this transverse direction.

8. The roll in accordance with claim 1, wherein the folded, Z-shaped configuration is secured to itself.

9. The roll in accordance with claim 1, wherein the folded, Z-shaped configuration is secured to itself by a plurality of discrete adhesion points, each with a cross-sectional area of less than 1 mm$^2$.

10. The roll in accordance with claim 1, wherein the extension of the specifically adherently configured first zone of the first section in the transverse direction corresponds essentially to the width of the folded, Z-shaped configuration.

11. The roll in accordance with claim 1, wherein the Z-shaped fold is such that the first zone and the second zone are furnished on the same visible side of the folded fastening element.

12. The roll in accordance with claim 1, wherein a thickness of the folded, Z-shaped configuration is greater than a thickness of the second section in the area of the second zone having the mechanically acting closures.

13. The roll in accordance with claim 1, wherein the continuous web is wound in such a way that a width of the roll is determined by the extension of the fastening elements in the transverse direction.

14. The roll in accordance with claim 1, wherein the continuous web is cross-wound so that a width of the roll is considerably greater than the extension of the fastening elements in the transverse direction.

15. The roll in accordance with claim 1, wherein at least the first zone of the first section is configured for an adhesive application and the first section is folded such that in the roll the adhesive application disposed in the first zone lies on a back side of the second section and can easily be detached therefrom when the web is unwound.

* * * * *